US012690920B2

(12) United States Patent
Jin et al.

(10) Patent No.: US 12,690,920 B2
(45) Date of Patent: Jul. 28, 2026

(54) COOLING SLEEVE AND OPTICAL FIBER CATHETER HAVING SAME

(71) Applicant: HANGZHOU GENLIGHT NEUROTECH CO., LTD., Zhejiang (CN)

(72) Inventors: Huijie Jin, Zhejiang (CN); Peng Cao, Zhejiang (CN); Liangdao Xia, Zhejiang (CN); Xinlei Chen, Zhejiang (CN); Xiangliang Liao, Zhejiang (CN)

(73) Assignee: HANGZHOU GENLIGHT NEUROTECH CO., LTD., Zhejiang (CN)

(*) Notice: Subject to any disclaimer, the term of this patent is extended or adjusted under 35 U.S.C. 154(b) by 250 days.

(21) Appl. No.: 18/287,076

(22) PCT Filed: Apr. 26, 2022

(86) PCT No.: PCT/CN2022/089280
§ 371 (c)(1),
(2) Date: Oct. 16, 2023

(87) PCT Pub. No.: WO2022/228428
PCT Pub. Date: Nov. 3, 2022

(65) Prior Publication Data
US 2024/0197398 A1     Jun. 20, 2024

(30) Foreign Application Priority Data

Apr. 30, 2021    (CN) ........................ 202110484230.X

(51) Int. Cl.
*A61B 18/24*     (2006.01)
*A61B 18/00*     (2006.01)

(52) U.S. Cl.
CPC .... *A61B 18/24* (2013.01); *A61B 2018/00023* (2013.01); *A61B 2018/00172* (2013.01); *A61B 2018/00577* (2013.01)

(58) Field of Classification Search
CPC .......... A61B 2018/00172; A61B 18/24; A61B 2018/00023
See application file for complete search history.

(56) References Cited

U.S. PATENT DOCUMENTS

| | | | |
|---|---|---|---|
| 5,827,267 A | 10/1998 | Savage et al. | |
| 7,127,033 B2 | 10/2006 | Lovoi et al. | |

(Continued)

FOREIGN PATENT DOCUMENTS

| | | |
|---|---|---|
| CN | 101969875 A | 2/2011 |
| CN | 104704311 A | 6/2015 |

(Continued)

OTHER PUBLICATIONS

Office action issued on Apr. 29, 2025 from China Patent Office in a counterpart China Patent Application No. 202110484230.X (all the cited references are listed in this IDS.) (English translation is also submitted herewith.).

(Continued)

*Primary Examiner* — Sung H Pak
(74) *Attorney, Agent, or Firm* — The PL Law Group, PLLC

(57)     ABSTRACT

A cooling sleeve includes an inner tube within which a bar-shaped or tubular object is placed to be cooled, and an outer tube within which the inner tube is located. The outer wall surface of the bar-shaped or tubular object contacts with the inner wall surface of the inner tube to form first contact portions, and axial gaps from the adjacent first contact portions form first circulation channels, and the inner wall surface of the outer tube contacts with the outer wall surface (Continued)

Distal End ⟵ ···································································· ⟶ Proximal End of the inner tube to form second contact portions, and axial gaps from the adjacent second contact portions form second circulation channels. Proximal ends of the first and second circulation channels are connected with each other inside the proximal end of the outer tube via a forming cavity, and distal ends of the first and second circulation channels are independently connected externally.

11 Claims, 8 Drawing Sheets

(56) References Cited

U.S. PATENT DOCUMENTS

| | | | |
|---|---|---|---|
| 8,123,789 B2 | 2/2012 | Khanna | |
| 2003/0199860 A1 | 10/2003 | Loeb et al. | |
| 2006/0217693 A1* | 9/2006 | Gowda | A61B 18/20 |
| | | | 606/15 |
| 2010/0292766 A1 | 11/2010 | Duong et al. | |
| 2017/0319267 A1* | 11/2017 | Dickhans | A61B 18/1477 |
| 2019/0350652 A1 | 11/2019 | Van Der Weide et al. | |

FOREIGN PATENT DOCUMENTS

| | | |
|---|---|---|
| CN | 107087399 A | 8/2017 |
| CN | 109009429 A | 12/2018 |
| CN | 111120755 A | 5/2020 |
| CN | 113081255 A | 7/2021 |
| CN | 113180823 A | 7/2021 |
| CN | 215425064 U | 1/2022 |

OTHER PUBLICATIONS

Office action issued on Jun. 26, 2025 from Vietnam Intellectual Property Office in a counterpart Vietnam Patent Application No. 1-2023-07257 (English translation is also submitted herewith.).

Communication pursuant to Article 94(3) EPC issued on Aug. 28, 2025 from European Patent Office in a counterpart European Patent Application No. 22794898.1.

Office action issued on Aug. 30, 2025 from China Patent Office in a counterpart China Patent Application No. 202110484230.X (English translation is also submitted herewith.).

International Search Report for PCT/CN2022/089280 mailed on Jul. 15, 2022.

European Search Report For EP 22794898.1 issued on Mar. 17, 2025 from European patent office in a counterpart European patent application (See the highlight sentences of Part 2, p. 2).

Office action issued on Oct. 21, 2025 from Korean Patent Office in a counterpart Korean Patent Application No. 10-2023-7038070 (all the cited references are listed in this IDS.) (English translation is also submitted herewith.).

Office action issued on Nov. 1, 2024 from China Patent Office in a counterpart China Patent Application No. 202110484230.X (all the cited references are listed in this IDS.) (English translation is also submitted herewith.).

Office action issued on Nov. 10, 2025 from Brazilian Patent Office in a counterpart Brazilian Patent Application No. BR112023022590-6 (all the cited references are listed in this IDS.) (English translation is also submitted herewith.).

* cited by examiner

COOLING SLEEVE AND OPTICAL FIBER CATHETER HAVING SAME

CROSS REFERENCE TO RELATED APPLICATIONS AND CLAIM OF PRIORITY

This application claims benefit under 35 U.S.C. 119, 120, 121, or 365(c), and is a National Stage entry from International Application No. PCT/CN2022/089280 filed on Apr. 26, 2022, which claims priority to the benefit of Chinese Patent Application No. 202110484230.X filed in the Chinese Intellectual Property Office on Apr. 30, 2021, the entire contents of which are incorporated herein by reference.

BACKGROUND

1. Technical Field

The present disclosure relates to the field of medical devices, particularly to a cooling sleeve and an optical fiber catheter having the same.

2. Background Art

Advances in modern cutting-edge science and technology have brought new developments in the diagnosis and treatment of intracranial tumors, and the survival expectations and survival rates of brain tumor patients have been greatly improved. Among them, Laser Interstitial Thermal Therapy (LITT) guided by Magnetic Resonance Imaging (MRI) has played a pivotal role. LITT is a kind of percutaneous minimally invasive surgery under stereotactic guidance, where lasers act on target points through optical fibers to selectively ablate pathological tissues. During surgery, light energy is transmitted to lesion tissues through optical fibers for precise irradiation, realizing photothermal conversion, thereby raising the temperature of the lesion area and leading to thermal coagulation necrosis of lesion tissues for therapeutic purposes. Relevant studies have shown that when tissue temperature exceeds 60° C., rapid coagulation necrosis and instantaneous cell death occur; at temperatures above 100° C., tissues vaporize, and at temperatures exceeding 300° C., tissues carbonize. Carbonized tissue hinders the penetration of light energy and the conduction of thermal energy, and can even damage the optical fiber. Moreover, the gases formed during tissue vaporization under high temperatures act as insulators, limiting thermal energy accumulation, so excessively high ablation temperatures should be avoided.

Currently, to better control ablation temperature, aside from regulating laser power, the temperature at the proximal end of the optical fiber is usually controlled by a closed-loop condensed liquid or gas to achieve cycle cooling. In essence, the proximal end of the optical fiber is provided with a cooling sleeve. The cooling sleeve usually includes an inner circulation pipeline and an outer circulation pipeline. The optical fiber is placed within the inner circulation pipeline. By utilizing the circulation of the cooling medium within the inner and outer circulation pipelines, heat from the proximal end of the optical fiber can be taken away, preventing damage of the optical fiber from high temperatures and overheat of the optical fiber, thereby ensuring surgical outcomes.

It is worth noting that another major factor affecting LITT is precision ablation, which encompasses not only accurate puncture positioning of the laser probe, but also precise positioning and stability of the proximal end of the optical fiber (i.e., the end closer to the lesion tissues). However, in existing optical fiber cooling systems, the proximal end of the optical fiber is completely exposed within the inner circulation pipeline without support and fixed. When the flow rate of the cooling medium flowing into the inner circulation pipeline is high, the proximal end of the optical fiber will inevitably oscillate, causing it to deviate from the central axis of the cooling sleeve, and even making its light emitting part to contact with the inner wall of the inner tube, which affects the stability and precision of laser output. Furthermore, existing inner circulation pipeline and outer circulation pipeline only rely on a fixed seat for single-point positioning, easily leading to device collision, deformation, or wear under external forces (e.g., during device transportation), thus increasing manufacturing cost. Additionally, the circulation pipelines through which the fluid flows in existing cooling sleeves are somewhat simplistic: when the flow rate of the cooling medium is relatively gentle, there might be a cross-flow phenomenon, affecting the cooling effect. Therefore, addressing the shortcomings and issues inherent in existing technologies to better and more swiftly advance LITT in the medical field is an urgent technical problem that professionals in this domain are keen on solving.

SUMMARY

The objective of the present disclosure is to provide a cooling sleeve, which consecutively contains, from inside to outside, an optical fiber, an inner tube and an outer tube. The coaxial self-arrangement-and-support among the three is realized through line contact or surface contact between the optical fiber and the inner tube, and between the inner tube and the outer tube. This design firmly secures the optical fiber within the inner tube, ensuring that the optical fiber, the inner tube and the outer tube always remain on the same axis. Another objective of the present disclosure is to provide an optical fiber catheter, which includes the cooling sleeve and a water-tight assembly. The water-tight assembly further clamps the outer tube, the inner tube and the optical fiber, ensuring even more precise positioning of the optical fiber catheter.

The technical solutions adopted in the present disclosure are as follows.

The cooling sleeve of the present disclosure includes an inner tube, and a bar-shaped or tubular object to be cooled is placed inside the inner tube. The outer wall surface of the bar-shaped or tubular object contacts with the inner wall surface of the inner tube, forming several first contact portions that extend in an axial direction. Axial gaps from the adjacent first contact portions form first circulation channels.

The cooling sleeve also includes an outer tube. The inner tube is located inside the outer tube. The inner wall surface of the outer tube contacts with the outer wall surface of the inner tube, forming several second contact portions that extend in the axial direction. Axial gaps from the adjacent second contact portions form second circulation channels.

Proximal ends of the first circulation channels and proximal ends of the second circulation channels are connected to each other inside the proximal end of the outer tube via a forming cavity: distal ends of the first circulation channels and distal ends of the second circulation channels are independently connected externally.

Further, the first contact portions and the second contact portions are arranged relative independently: the first contact portions are in line contact or surface contact manner, and the second contact portions are also in line contact or surface contact manner.

Further, both the first contact portions and the second contact portions are in line contact manner; the first contact portions include at least 3 first line contact portions, and the second contact portions include at least 3 second line contact portions.

Further, cross sections of the inner tube and the outer tube are both polygonal: or the cross section of the inner tube is polygonal while the cross section of the outer tube is circular or quasi-circular.

Further, the bar-shaped or tubular object is an optical fiber, and the optical fiber, the inner tube and the outer tube are arranged coaxially: the proximal end of the optical fiber is located within the proximal end of the inner tube, and the distal end of the optical fiber is located outside the distal end of the inner tube, and the distal end of the inner tube is located outside the distal end of the outer tube; the distal end of the inner tube connects to an inlet pipeline, and the distal end of the outer tube connects to an outlet pipeline.

Further, the inlet pipeline is equipped with a pump and cooling liquid; the outlet pipeline is attached with a waste liquid container.

Further, the cooling liquid is stored in a coolant tank, and a thermostatic heating device is equipped either inside or outside the coolant tank.

The present disclosure also provides an optical fiber catheter, which includes the aforementioned cooling sleeve and a water-tight assembly arranged on the outer periphery of the cooling sleeve: the water-tight assembly includes a pipe body and a tubular connector. A first connection part is provided on a connection port of the pipe body: a branch tube connected externally is also provided on the pipe body. A second connection part is provided on the tubular connector. The tubular connector is fixedly connected to the pipe body through the second connection part and the first connection part.

Further, the connecting manner of the first connection part and the second connection part may include one of the following: screw connection, flange connection, welding, clamp connection, ferrule connection, crimp connection, hot melt connection and clamp-fixed connection.

Further, the first connection part is a protruding connection part provided on an outer peripheral wall of the connection port: the second connection part is a notch connection slot provided on the tubular connector: the tubular connector is fixedly connected to the pipe body through the notch connection slot and the protruding connection part.

Further, the water-tight assembly includes at least 2 aforementioned pipe bodies and 1 aforementioned tubular connector: an outer diameter of the pipe body fits the inner diameter of the tubular connector, and the tubular connector is clamped at a butt joint of the pipe bodies. In addition, a bridging sealing plug is provided at the butt joint of the pipe bodies: a center hole of the bridging sealing plug fits the inner tube.

Further, a distal sealing plug is provided inside a connection port at the distal end of the water-tight assembly, and a proximal sealing plug is provided inside a connection port at the proximal end of the water-tight assembly: a central hole of the distal sealing plug fits the optical fiber and a central hole of the proximal sealing plug fits the outer tube.

The optical fiber, the pipe body, the distal sealing plug and the bridging sealing plug are sealed to form an inlet-type cavity that only connects to the inner tube: the inner tube, the pipe body, the bridging sealing plug and the proximal sealing plug are sealed to form an outlet-type cavity that only connects with the outer tube.

Further, the inlet-type cavity connects to the inlet pipeline, which is equipped with a pump and a coolant tank: the outlet-type cavity connects to the outlet pipeline which is attached with a waste liquid container.

Further, a thermostatic heating device is provided either inside or outside the coolant tank.

Compared with the prior art, the present disclosure achieves the following beneficial effects through the ingenious structural design:

(1) The positional relationship between the optical fiber, the inner tube and the outer tube can be firmly fixed together, ensuring their coaxiality and straightness. The reliable assembly relationship of the three also greatly reduces the volume of the optical fiber catheter, making its insertion into the human body/brain less traumatic and safer.

(2) Multiple fluid-type cavities ensure that there is no cross-flow between the inflow and outflow fluids, resulting in better cooling effects, and more precise control of the ablation temperature of the optical fiber.

(3) Moreover, the optical fiber catheter described in the present disclosure also includes a water-tight assembly, which exerts both radial and axial forces, further clamping the outer tube, the inner tube and the optical fiber, greatly ensuring the precise positioning effect of the optic fiber catheter.

(4) In addition, the present disclosure also provides various embodiments of the assembly relationship between the inner tube and the outer tube for flexible selection by those skilled in the art or medical workers during actual operations. Moreover, in the preferred embodiment of the present disclosure, the outer tube is cylindrical; while the inner tube has a different shape (i.e., the cross section of the inner tube is non-circular), making it easier to confirm the state of the inner tube in a fixed direction, preventing the inner tube from rotating.

(5) The sealing materials between the parts of the present disclosure are preferably made of soft silicone material, which achieves a sealing effect through deformation and compression of the materials, ensuring effective sealing.

(6) In a preferred embodiment of the present disclosure, all parts of the water-tight assembly can preferably be connected using a threaded structure. Its fastening effect is adjustable, the installation process is smooth, and it avoids issues with product quality due to varying tolerance gaps in batch components, which is conducive to standardized production.

DETAILED DESCRIPTION

A cooling sleeve proposed by the present disclosure comprises, from inside to outside in sequence, a bar-shaped or tubular object to be cooled, an inner tube and an outer tube. The key lies in the assembly design of these three components, where the bar-shaped or tubular object to be cooled, the inner tube and the outer tube make contact through line or surface contact, or a mixed alternating mode of line contact and surface contact. Such an arrangement allows for coaxial self-arrangement-and-support among the three components without the need for additional supporting structures. Moreover, multiple fluid cavities formed by this structure also avoid the cross-flow phenomenon of the fluids and ensure the cooling effect of the cooling sleeve.

In the context of Magnetic Resonance Imaging (MRI) guided Laser Interstitial Thermal Therapy (LITT), the bar-shaped or tubular object to be cooled in the cooling sleeve of this disclosure refers to an optical fiber. The following will take LITT technology as the creation background and describe the present invention in detail in conjunction with the accompanying drawings and specific embodiments. The illustrative examples and descriptions provided are only to explain this invention and are not intended to limit it. Furthermore, to clarify the present invention's description, the "proximal end" mentioned in this disclosure refers to the end of the ablation device or optical fiber closer to the lesion tissue, while the end further from the lesion tissue is referred to as the "distal end".

Figure 1:
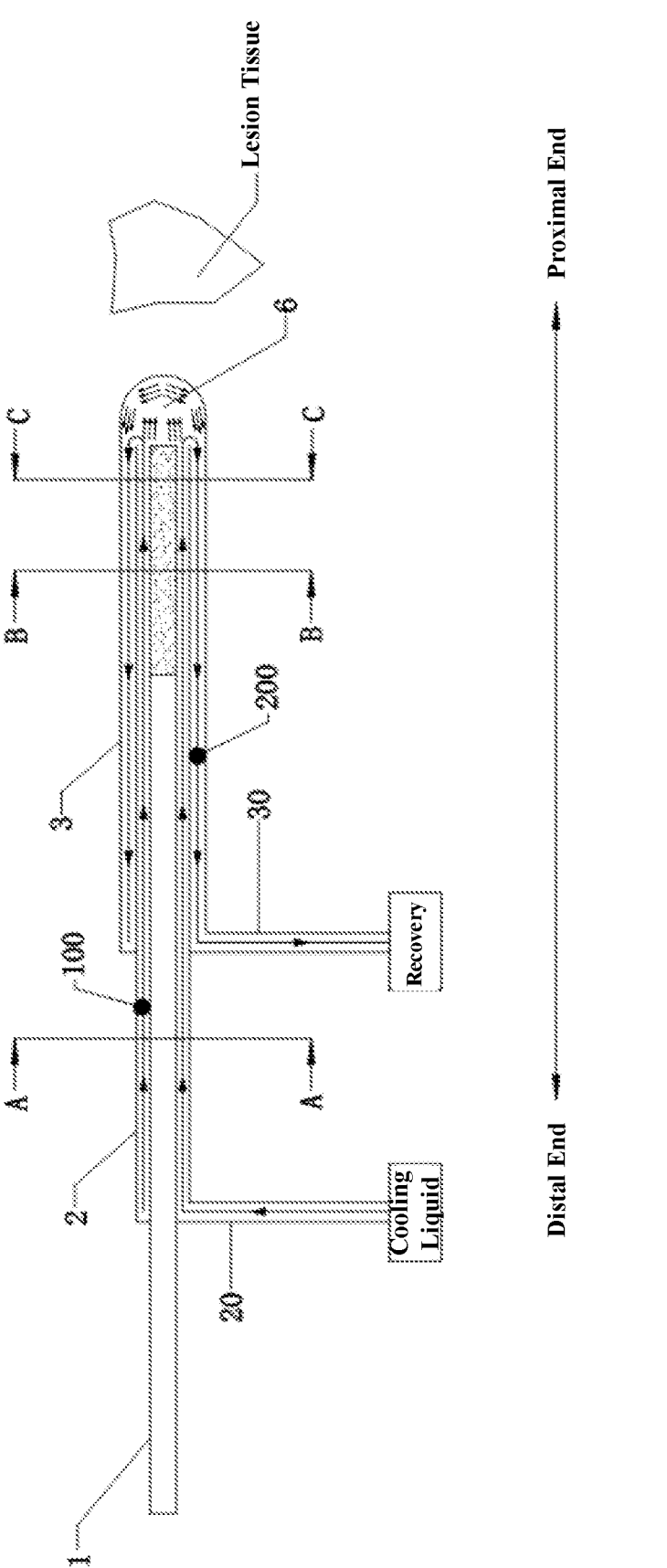
FIG. 1 is a schematic illustration of a simplified structure of the cooling sleeve.
Figure 2:
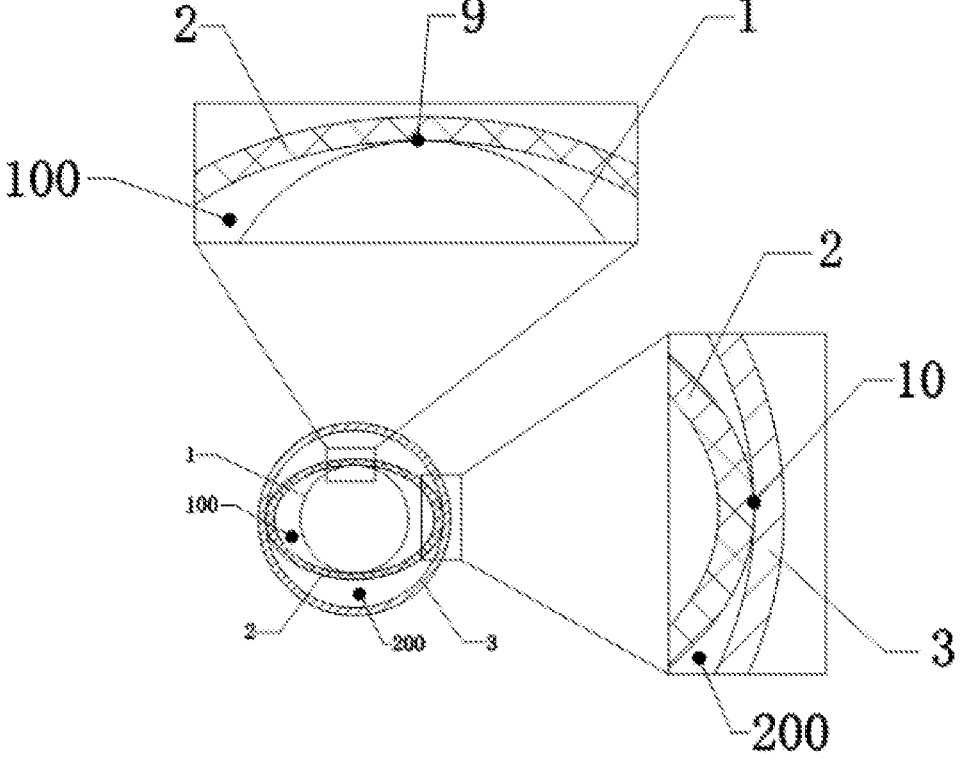
FIG. 2 is a sectional view along line C-C in FIG. 1.

As shown in FIGS. 1 and 2, which depict a schematic diagram of the basic structure of the cooling sleeve and a sectional view along line C-C in FIG. 1, respectively, the cooling sleeve includes an optical fiber 1 and an inner tube 2. The optical fiber 1 is located within the inner tube 2, and the outer wall surface of the optical fiber 1 is in partial contact with the inner wall surface of the inner tube 2 to form several first contact portions 9 extending in the axial direction. Axial gaps from these adjacent first contact portions 9 form first circulation channels 100. The cooling sleeve further includes an outer tube 3, the cross-sectional shape of which can be the same or different from the inner tube 2. The inner tube 2 is located within the outer tube 3, and the inner wall surface of the outer tube 3 is in partial contact with the outer wall surface of the inner tube 2 to form several second contact portions 10 extending in the axial direction. Axial gaps from these adjacent second contact portions 10 form second circulation channels 200. Proximal ends of the first circulation channels 100 and proximal ends of the second circulation channels 200 are connected with each other inside the proximal end of the outer tube 3 via a forming cavity 6; distal ends of the first circulation channels 100 and distal ends of the second circulation channels 200 are independently connected externally.

Further, the first contact portions 9 and the second contact portions 10 are preferably arranged relative independently. The first contact portions can be in line contact or surface contact manner, and the second contact portions can also be in line contact or surface contact manner. Alternatively, the first contact portions can have a mixed form of line contact and surface contact, and the second contact portions can also have a mixed form of line contact and surface contact. Within the same cooling sleeve, the contact manners of the first contact portions and the second contact portions can both be the line contacts, or both be the surface contacts, or a mixed form of line contact and surface contact. Or, other combined contact manners that can realize the present disclosure could be considered. Regardless of the manner of contact, any equivalent transformations and modifications made within the scope of the present disclosure will be protected by it.

Please also refer to FIGS. 3A-3H, and FIGS. 4A-4H, which are cross-sectional views of the section A-A and section B-B in FIG. 1, respectively. These figures clearly show the contact manners, assembly relationship and cross-sectional shapes between the optical fiber 1 and the inner tube 2, and between the inner tube 2 and the outer tube 3. The specifics are described below:

[Case 1]: As shown in FIGS. 3A-3E and FIG. 3H, in a preferred embodiment of the present disclosure, the first contact portions 9 may be formed when the outer wall surface of the optical fiber 1 contacts the inner wall surface of the inner tube 2 in a line contact manner, thereby forming several first line contact portions extending along the length direction of the inner tube 2 (e.g., there are 3 first line contact portions in FIGS. 3A, and 7 first line contact portions in FIG. 3E). Concurrently, several axial gaps from the adjacent first line contact portions collectively constitute first circulation channels 100, which allow fluid to flow through.

Figures 3A, 3B, 3C, 3D, 3E, 3F, 3G, 3H:
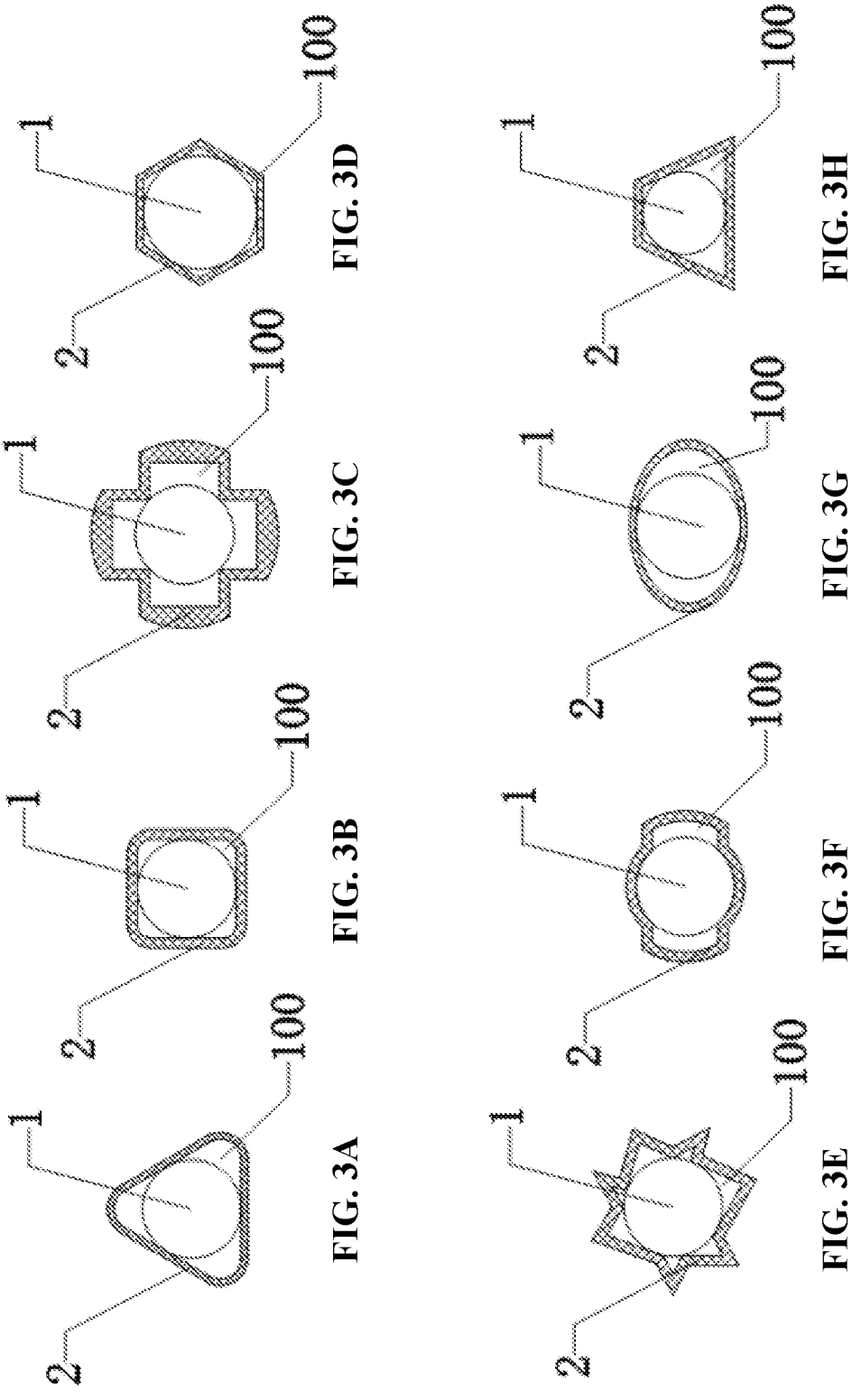
FIGS. 3A to 3H are sectional views along line A-A in FIG. 1.

[Case 2]: As shown in FIGS. 3F-3G, in another preferred embodiment of the present disclosure, the first contact portions 9 can also be formed when the outer wall surface of the optical fiber 1 contacts the inner wall surface of the inner tube 2 in a surface contact manner, thereby forming at least several first surface contact portions extending along the length direction of the inner tube 2 (e.g., there are 2 first surface contact portions in both FIG. 3F and FIG. 3G). Similarly, several axial gaps from the adjacent first surface contact portions collectively constitute first circulation channels 100, which allow fluid to flow through.

[Case 3]: As shown in FIGS. 4A-4C and FIGS. 4F-4G, the second contact portions 10 may be formed when the inner wall surface of the outer tube 3 contacts the outer wall surface of the inner tube 2 in a surface contact manner, thereby forming several second surface contact portions extending along the length direction of the outer tube 3 (e.g., there are 3 second surface contact portions in FIGS. 4A and 2 second surface contact portions in FIG. 4F). Meanwhile, axial gaps from the adjacent second surface contact portions collectively constitute second circulation channels 200, which allow fluid to flow through.

Figures 4A, 4B, 4C, 4D, 4E, 4F, 4G, 4H:
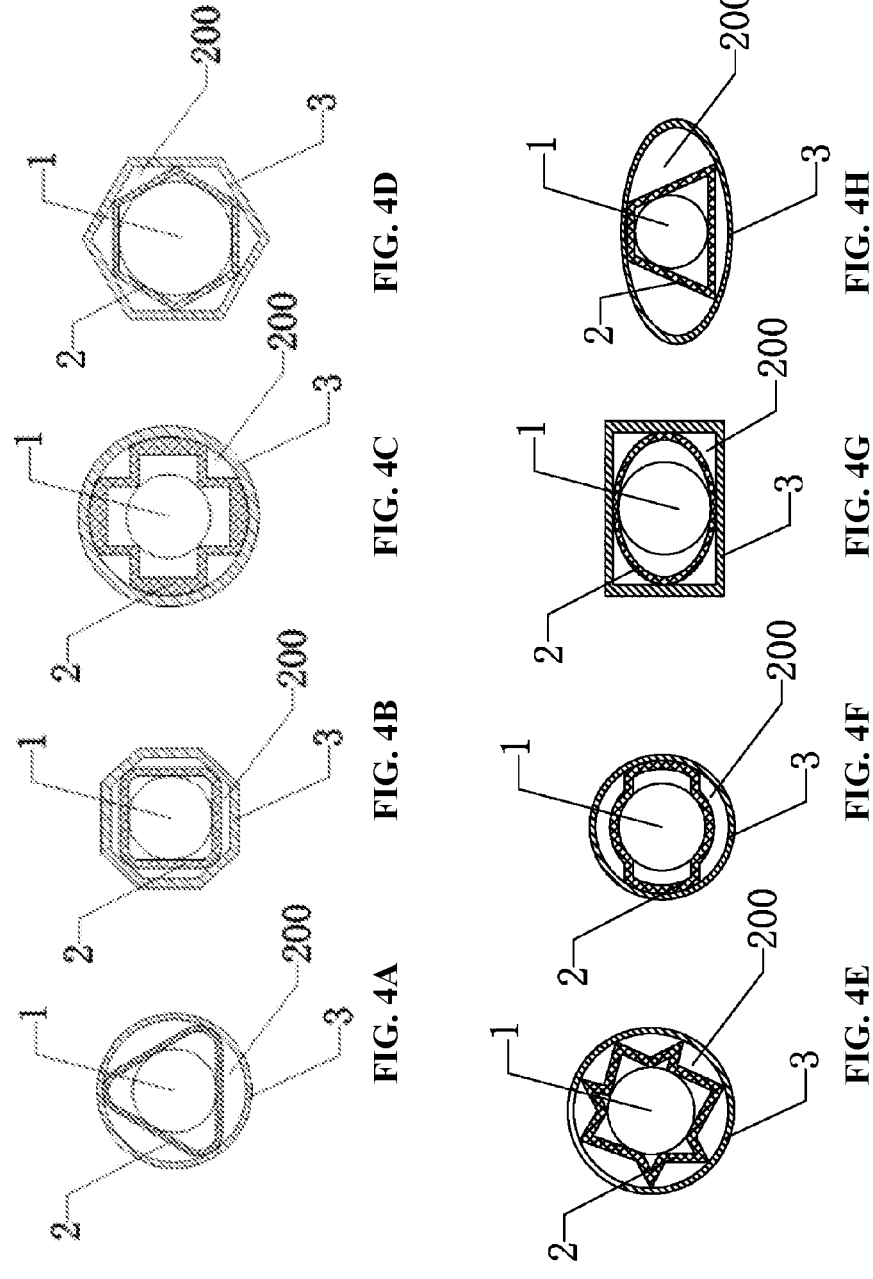
FIGS. 4A to 4H are sectional views along line B-B in FIG. 1.

[Case 4]: As shown in FIG. 4D, FIG. 4E, and FIG. 4H, the second contact portions 10 can also be formed when the inner wall surface of the outer tube 3 contacts the outer wall surface of the inner tube 2 in a line contact manner, thereby forming several second line contact portions extending along the length direction of the outer tube 3 (e.g., there are 6 second line contact portions in FIGS. 4D and 4 second line contact portions in FIG. 4H). Similarly, axial gaps from the adjacent second line contact portions collectively constitute second circulation channels 200, which allow fluid to flow through.

Preferably, the optical fiber 1, the inner tube 2 and the outer tube 3 are arranged coaxially. The several axial gaps are preferably distributed evenly along the circumferential direction. Moreover, the first circulation channels 100 and the second circulation channels 200 are preferably arranged alternately. With such an arrangement, the temperature of the optical fiber located at the position of the first contact portions 9 is controlled and cooled by the cooling medium flowing through the second circulation channel 200, while the temperature of the optical fiber located at the position of the second contact portions 10 is controlled and cooled by the cooling medium flowing through the first circulation channels 100. That is, the cooling channels flowing through the inner tube (referred to in this disclosure as the first circulation channels) and the cooling channels flowing through the outer tube (referred to in this disclosure as the second circulation channels) should be staggered to ensure circumferential cooling. This not only ensures that the optical fiber, the inner tube, and the outer tube achieve coaxial self-arrangement-and-support, ensuring the optical fiber remains stable and firm during operation, but also ensures effective cooling of the optical fiber's periphery, ensuring the cooling capability of the cooling sleeve. Additionally, the configuration of the optical fiber, the inner tube, and the outer tube in this disclosure significantly reduces the size of the ablation device, benefiting minimally invasive surgical procedures.

Please refer to FIG. 3A to FIG. 3H and FIG. 4A to FIG. 4H again, which are cross-sectional views of sections A-A and B-B in FIG. 1, respectively. The present disclosure also presents or provides various types of inner and outer tubes. For example, the cross-sectional shape of the inner tube 2 may be circular, quasi-circular or polygonal; the cross-sectional shape of the outer tube 3 may also be circular, quasi-circular or polygonal. Moreover, the inner tube 2 and the outer tube 3 can also have the same cross-sectional shape, for example, as shown in FIG. 4D, both the inner tube 2 and the outer tube 3 have a hexagonal cross section. In addition, in practical application, operators can adjust the shape or contact manner of the contact points (i.e., the first contact portions and the second contact portions) to adjust the cross-sectional area ratio of the first circulation channels and the second circulation channels, to make the flow more uniform. For example, in FIG. 4A, there is three-sided contact, allowing for increased fluid flow space inside, while in FIG. 4F, only two sides are in contact, providing even more fluid flow space.

Figure 5:
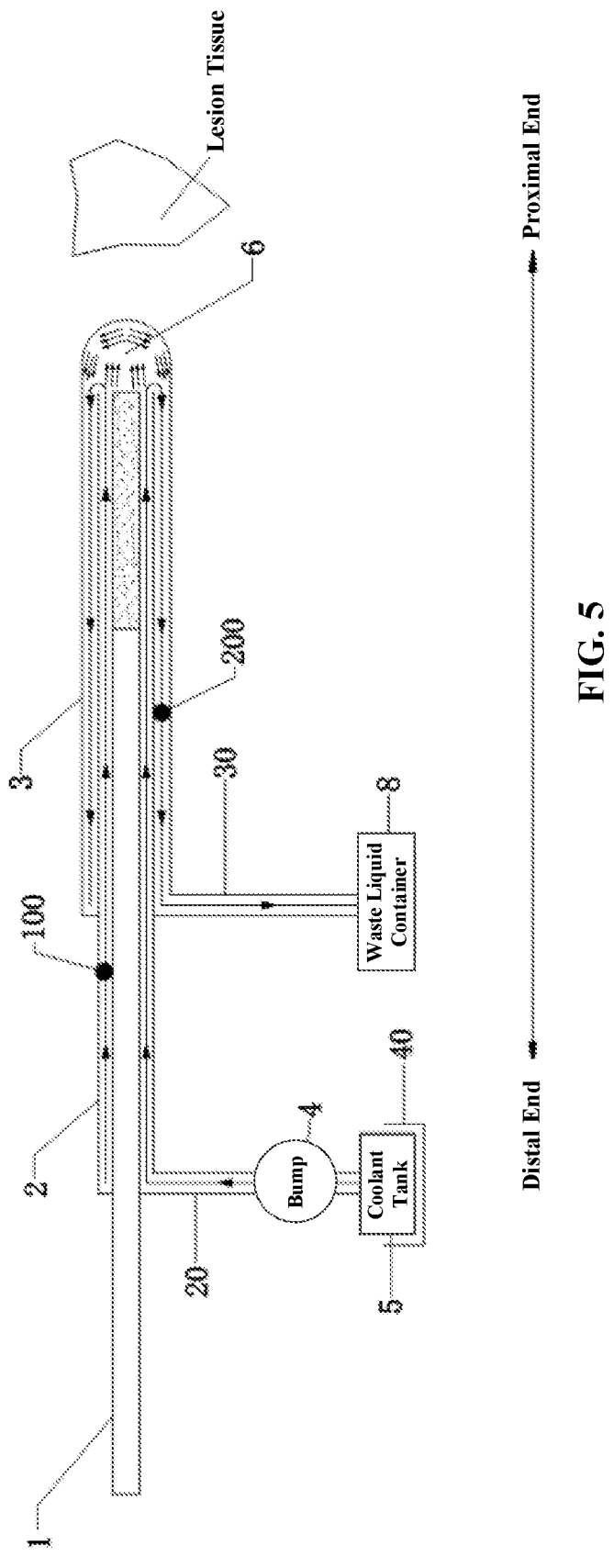
FIG. 5 illustrates the structure of a preferred embodiment of the cooling sleeve of the present disclosure.

Please refer to FIG. 5, which is a schematic structural diagram of the cooling sleeve in a preferred embodiment of the present disclosure. In this embodiment, the optical fiber 1, the inner tube 2 and the outer tube 3 are arranged coaxially: and the proximal end of the optical fiber 1 is located within the proximal end of the inner tube 2, and the distal end of optical fiber 1 is far beyond the distal end of the inner tube 2, and the distal end of the inner tube 2 is located outside the distal end of the outer tube 3. The proximal end of the inner tube 2 connects with the proximal end of the outer tube 3 via a forming cavity 6. The distal end of the inner tube 2 is connected to an inlet pipeline 20, and the distal end of the outer tube 3 is connected to an outlet pipeline 30.

Figure 6:
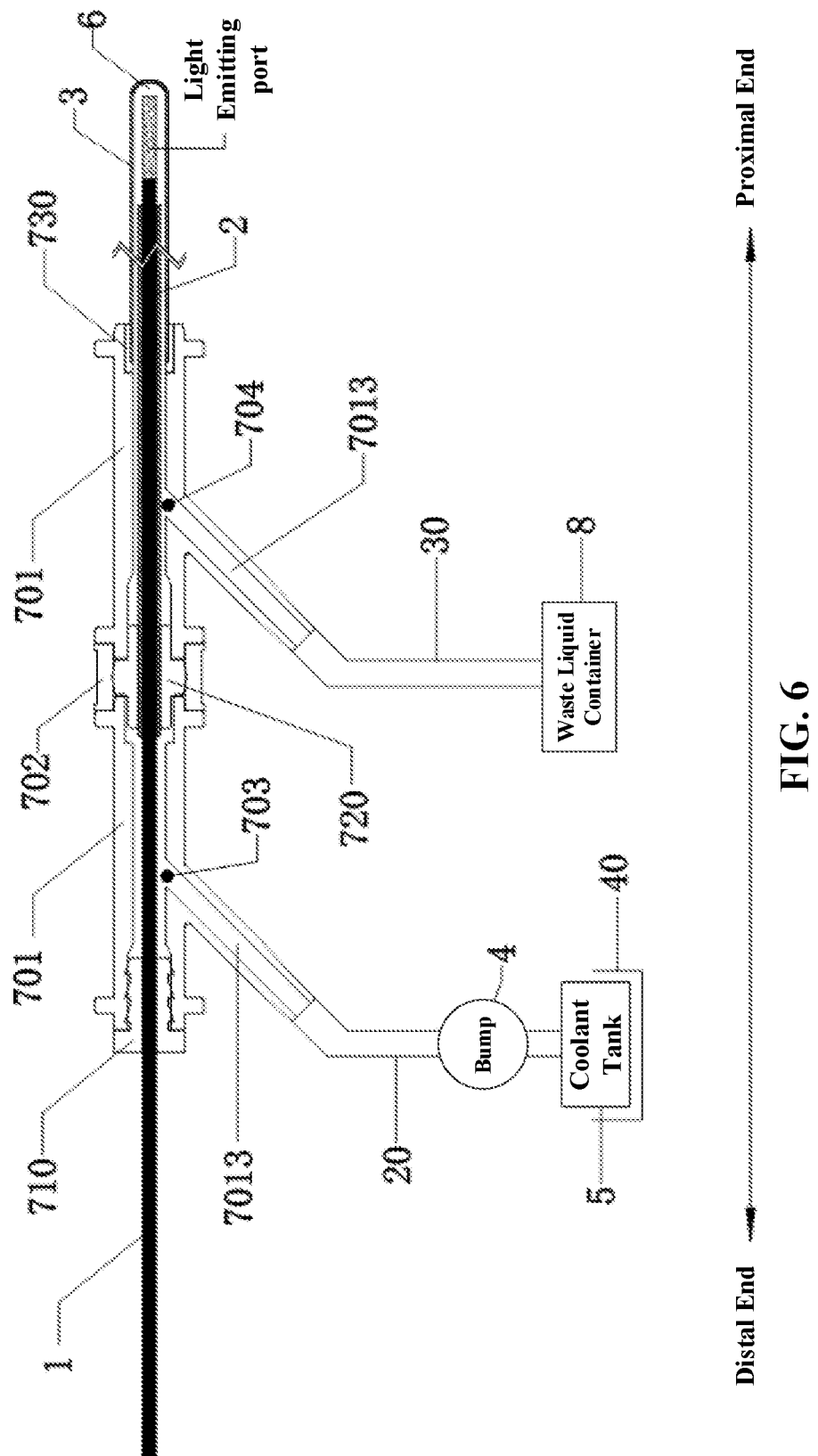
FIG. 6 is a schematic illustration of the optical fiber catheter.

Further, the inner tube 2 is preferably a tubular structure with openings at both ends. The proximal end of the optical fiber 1 (generally provided with a light emitting part, as shown in FIG. 6) can either be located within the proximal end of the inner tube 2 or partially extend out of the proximal end of inner tube 2, with part of the proximal end of the optical fiber 1 retained within the forming cavity 6. The outer tube 3 is generally selected as a tube with one end open and the other end closed. The proximal end of the outer tube 3 is the closed end of the outer tube 3. The closed end is generally designed as a structure with a certain curvature or radius. Preferably, the closed end of the outer tube 3 has a spherical structure, to facilitate the directional return of the cooling medium (such as saline), reducing the occurrence of turbulence.

Referring again to FIG. 5, the inlet pipeline 20 is equipped with a pump 4 and cooling liquid, with the pump 4 preferably being a peristaltic pump, and the cooling liquid is stored in a coolant tank 5. A thermostatic heating device 40 is equipped either inside or outside the coolant tank 5. Alternatively, based on actual needs, the thermostatic heating device 40 can be arranged both inside and outside the coolant tank 5, to heat the cooling liquid to a temperature suitable for the human body, preventing irritation to tissues when the cooling fluid flows through them. Further, the outlet pipeline 30 is attached with a device for recovering the cooling liquid, which can generally be set up as a waste liquid container 8.

The present disclosure also provides an optical fiber catheter, which is convenient for operators to use during operation. As shown in FIG. 6, it is a schematic diagram of the structure of the optical fiber catheter. The optical fiber catheter mainly includes a cooling sleeve and a water-tight assembly 7 arranged on the outer periphery of the distal end of the cooling sleeve. The shape and other characteristics of the cooling sleeve have been described in detail above, and will not be repeated here. The specific structural features of the water-tight assembly 7 will be described in detail below with reference to the drawings and specific embodiments.

Generally, the water-tight assembly 7 includes a pipe body 701 and a tubular connector 702. A first connection part is provided on a connection port 7011 of the pipe body 701. A branch tube 7013 connected externally is also provided on the pipe body 701. A second connection part is provided on the tubular connector 702. The second connection part matches the first connection part, and the tubular connector 702 is fixedly connected to the pipe body 701 through the second connection part and the first connection part. The connecting manner of the first connection part and the second connection part includes but is not limited to screw connection, flange connection, welding, clamp connection, ferrule connection, crimp connection, hot melt connection and clamp-fixed connection. In actual use, to facilitate standardized production of products, the fixing manner between the first connection part and the second connection part can preferably adopt a threaded structure. This threaded connection makes it easier to control the gap between parts, and is also easy to disassemble and adjust. Furthermore, the threaded connection prevents the seal from twisting during assembly, ensures concentricity among a front pipe body and a rear pipe body and a tubular connector therebetween, and avoids uneven gaps and uneven force caused by twisting. The risk of leakage is further reduced, and the yield rate of products is improved.

Figure 7:
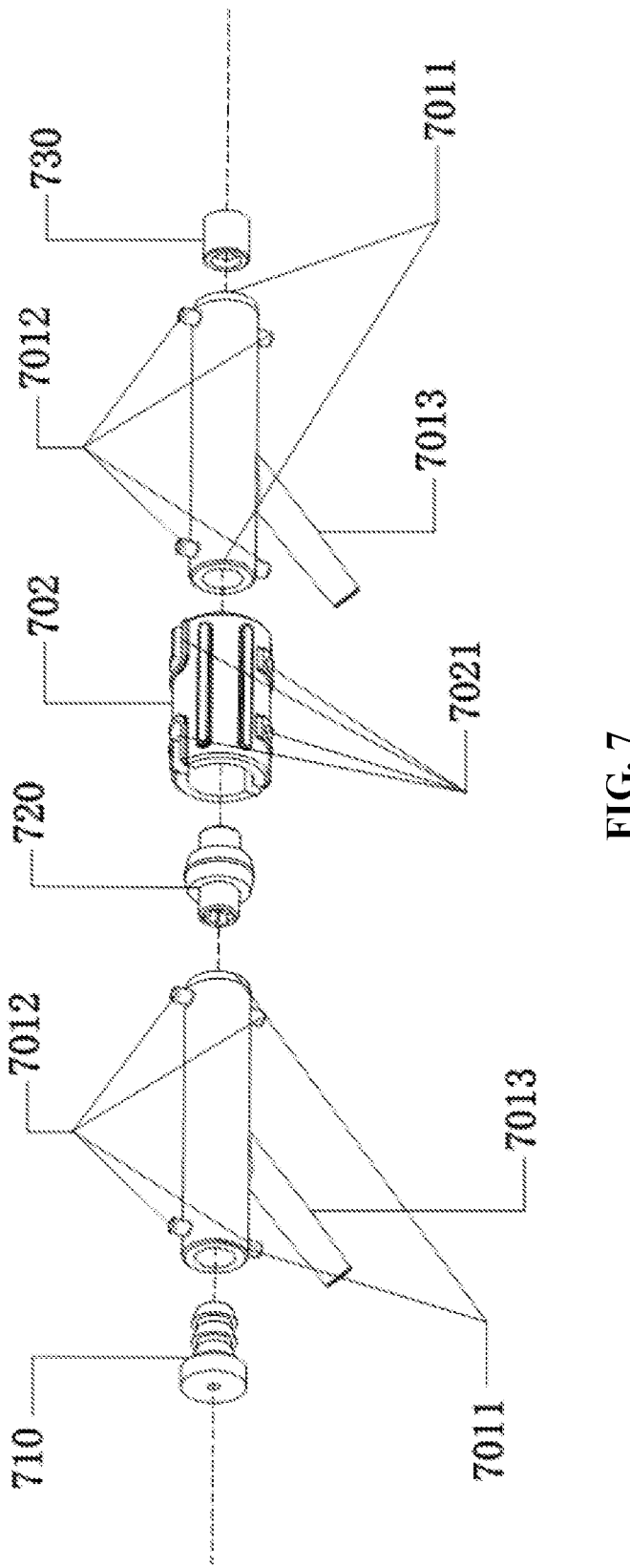
FIG. 7 depicts the structure of the water-tight assembly.
Figures 8A, 8B, 8C, 8D, 8E, 8F:
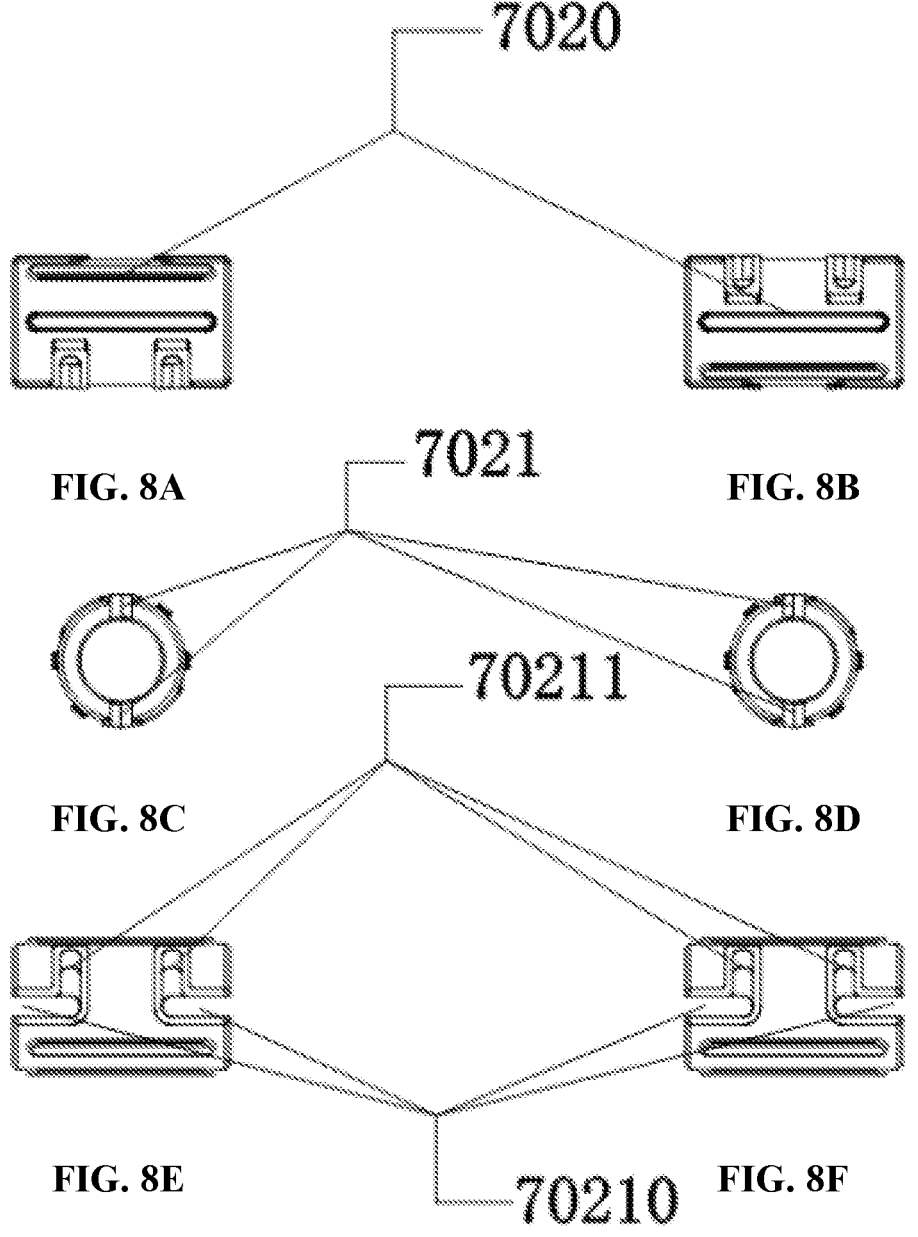
FIGS. 8A to 8F provide six-sided views of the tubular connector.

Please refer to FIG. 7, which is a structural schematic diagram of the water-tight assembly. In a preferred embodiment of the present disclosure, the water-tight assembly 7 includes a pipe body 701, and the parts used for connection at both ends of the pipe body 701 are the connection ports 7011. At least one protruding connection part 7012 (i.e., the first connection part described in the present disclosure) is provided on the peripheral wall of the connecting port 7011. The pipe body 701 also has a branch tube 7013 on one side that connects externally.

Please also refer to FIG. 8A to FIG. 8F, which are six-sided views of the tubular connector. The water-tight assembly 7 also includes a tubular connector 702. Notch connection slots 7021 (i.e., the second connection part described in the present disclosure) are respectively provided near both ends of the tubular connector 702. Preferably, the notch connection slot 7021 is L-shaped, and the L-shaped notch connection slot 7021 includes an entrance part 70210 and a limiting part 70211. The tubular connector 702 can be firmly connected to the pipe body 701 through the notch connection slots 7021 and the protruding connection parts 7012. Furthermore, several reinforcing ribs 7020 may be added to the outer surface of the tubular connector 702, thereby greatly improving the impact resistance and durability of the tubular connector 702.

In a preferred embodiment of the optical fiber catheter of the present disclosure, the inner tube 2 has an open structure at both ends, while the outer tube 3 has one open end and one closed end. During use, the optical fiber 1, the inner tube 2 and the outer tube 3 are arranged coaxially, the proximal end of the optical fiber 1 is partially located outside the proximal end of the inner tube 2, the distal end of the optical fiber 1 is far beyond the distal end of the inner tube 2, and the distal end of the inner tube 2 is located outside the distal end of the outer tube 3. The proximal end of the inner tube 2 and the proximal end of the outer tube 3 are connected with each other via the forming cavity 6.

In addition, in this embodiment, a water-tight assembly 7 is also provided. The water-tight assembly 7 includes at least two (2) pipe bodies 701 and one (1) tubular connector 702, and the outer diameter of the pipe body 701 fits the inner diameter of the tubular connector 702. The tubular connector 702 is clamped at a butt joint of the two pipe bodies 701, that is, the notch connection slots 7021 on the tubular connector 702 fits the protruding connection parts 7012 on the pipe bodies 701, facilitating the clamp connection of the tubular connector 702 and the pipe bodies 701.

Further, a seal is provided between the cooling sleeve and the water-tight assembly 7. The seal includes a bridging sealing plug 720 set at the butt joint of the two pipe bodies 701, a distal sealing plug 710 located inside a connection port 7011 at the distal end of the water-tight assembly 7, and a proximal sealing plug 730 located inside a connection port 7011 at the proximal end of the water-tight assembly 7. The butt joint of the two pipe bodies 701 is preferably arranged at a position close to the distal end of the inner tube 2; that is, the bridging sealing plug 720 is preferably set inside the two connection ports 7011 at the butt joint of the two pipe bodies 701. Moreover, the inner diameter of a central hole of the bridging sealing plug 720 fits the outer diameter of the inner tube 2: the central hole of the distal sealing plug 710 fits the optical fiber 1, and the central hole of the proximal sealing plug 730 fits the outer tube 3.

Furthermore, the outer wall of the optical fiber 1, the inner wall of the pipe body 701 (referring to the pipe body near the distal end of the cooling sleeve), the distal sealing plug 710 and the bridging sealing plug 720 can be sealed to form an inlet-type cavity that only connects to the inner tube 2. The inlet-type cavity is connected to the inlet pipeline 20, and the inlet pipeline 20 is equipped with a pump 4 and a coolant tank 5. A thermostatic heating device 40 is provided either inside or outside the coolant tank 5. The thermostatic heating device 40 can be used to heat the cooling medium to a temperature suitable for the human body, preventing irritation to tissues when the cooling fluid flows through them. Preferably, the thermostatic heating device 40 ensures that the temperature of the cooling liquid in contact with human tissue is maintained at around 37.2° C., so as to avoid tissue reactions caused by a large temperature difference. Correspondingly, the outer wall of the inner tube 2, the outer wall of the pipe body 701 (referring to the one closer to the proximal end of the cooling sleeve), the bridging sealing plug 720 and the proximal sealing plug 730 can be sealed to form an outlet-type cavity 704 that only connects to the outer tube 3. The outlet-type cavity 704 is connected to the outlet pipeline 30, and the outlet pipeline 30 is attached with a waste liquid container 8.

The materials for the distal sealing plug 710, the bridging sealing plug 720 and the proximal sealing plug 730 are preferably soft silicone materials. The sealing effect is achieved through deformation and extrusion of the materials, ensuring a good sealing result. While ensuring the sealing properties, the materials for the inner tube and the outer tube can be made of glass with better light transmittance, enhancing the efficiency of the laser. Of course, resin materials can also be chosen, offering a wider range of choices and easier implementation.

The above descriptions are only exemplary embodiments of the present disclosure and do not limit the patent scope of this disclosure. Any equivalent structure or equivalent process changes based on the content of the specification and drawings of this disclosure, or those applied directly or indirectly in other related technical fields, are all similarly included within the scope of patent protection of this disclosure.

What is claimed is:

1. An optical fiber catheter, comprising:
   a cooling sleeve; and
   a water-tight assembly arranged on an outer periphery of the cooling sleeve, the water-tight assembly comprising:
   a pipe body, whose connection port is provided with a first connection part, and the first connection part is a protruding connection part provided on an outer peripheral wall of the connection port; and the pipe body further has a branch tube connected externally;
   a tubular connector, which has a second connection part, and the second connection part is a notch connection slot provided on the tubular connector; and
   the tubular connector is fixedly connected to the pipe body through the notch connection slot and the protruding connection part; and wherein the cooling sleeve comprises:
   an inner tube, within which a bar-shaped or tubular object is placed to be cooled, wherein the outer wall surface of the bar-shaped or tubular object contacts with the inner wall surface of the inner tube to form several first contact portions extending in an axial direction, and axial gaps from the adjacent first contact portions form first circulation channels; and
   an outer tube, within which the inner tube is located, wherein the inner wall surface of the outer tube contacts with the outer wall surface of the inner tube to form several second contact portions extending in the axial direction, and axial gaps from the adjacent second contact portions form second circulation channels,
   wherein proximal ends of the first circulation channels and proximal ends of the second circulation channels are connected with each other inside the proximal end of the outer tube via a forming cavity, and distal ends of the first circulation channels and distal ends of the second circulation channels are independently connected externally.

2. The optical fiber catheter according to claim 1, wherein the water-tight assembly includes at least two said pipe bodies and one said tubular connector;
   an outer diameter of the pipe body fits the inner diameter of the tubular connector, and the tubular connector is clamped at a butt joint of the pipe bodies; and
   a bridging sealing plug is further provided at the butt joint of the pipe bodies; and a center hole of the bridging sealing plug fits the inner tube.

3. The optical fiber catheter according to claim 2, wherein, a distal sealing plug is provided inside a connection port at the distal end of the water-tight assembly, a proximal sealing plug is provided inside a connection port at the proximal end of the water-tight assembly, a central hole of the distal sealing plug fits the optical fiber, a central hole of the proximal sealing plug fits the outer tube; and the optical fiber, the pipe body, the distal sealing plug and the bridging sealing plug are sealed to form an inlet-type cavity that only connects to the inner tube; the inner tube, the pipe body, the bridging sealing plug and the proximal sealing plug are sealed to form an outlet-type cavity that only connects with the outer tube.

4. The optical fiber catheter according to claim 3, wherein, the inlet-type cavity connects to the inlet pipeline which is equipped with a pump and a coolant tank; the outlet-type cavity connects with the outlet pipeline which is attached with a waste liquid container.

5. The optical fiber catheter according to claim 4, wherein, a thermostatic heating device is further provided either inside or outside the coolant tank.

6. The optical fiber catheter according to claim 1, wherein, the first contact portions and the second contact portions are arranged relative independently;

the first contact portions are in line contact or surface contact manner, and the second contact portions are in line contact or surface contact manner.

7. The optical fiber catheter according to claim 6, wherein, both the first contact portions and the second contact portions are in line contact manner; the first contact portions include at least 3 first line contact portions, and the second contact portions include at least 3 second line contact portions.

8. The optical fiber catheter according to claim 7, wherein, cross sections of the inner tube and the outer tube are both polygonal; or the cross section of the inner tube is polygonal, while the cross section of the outer tube is circular or quasi-circular.

9. The optical fiber catheter according to claim 8, wherein, the bar-shaped or tubular object is an optical fiber, the optical fiber, the inner tube and the outer tube are arranged coaxially; the proximal end of the optical fiber is located within the proximal end of the inner tube, the distal end of the optical fiber is located outside the distal end of the inner tube, and the distal end of the inner tube is located outside the distal end of the outer tube; and the distal end of the inner tube connects to an inlet pipeline, and the distal end of the outer tube connects to an outlet pipeline.

10. The optical fiber catheter according to claim 9, wherein the inlet pipeline is equipped with a pump and cooling liquid; and the outlet pipeline is attached with a waste liquid container.

11. The optical fiber catheter according to claim 10, wherein, the cooling liquid is stored by a coolant tank, and a thermostatic heating device is equipped inside or outside the coolant tank.

* * * * *